United States Patent
Suzumura

(10) Patent No.: US 8,394,827 B2
(45) Date of Patent: Mar. 12, 2013

(54) INHIBITOR OF THE DIFFERENTIATION OF T CELLS INTO TH1 CELLS

(75) Inventor: Akio Suzumura, Nagoya (JP)

(73) Assignees: Kowa Co., Ltd., Nagoya-shi (JP); National University Corporation Nagoya University, Nagoya-shi (JP)

( * ) Notice: Subject to any disclaimer, the term of this patent is extended or adjusted under 35 U.S.C. 154(b) by 424 days.

(21) Appl. No.: 12/669,865

(22) PCT Filed: Jul. 18, 2008

(86) PCT No.: PCT/JP2008/001924
§ 371 (c)(1), (2), (4) Date: Jan. 20, 2010

(87) PCT Pub. No.: WO2009/013885
PCT Pub. Date: Jan. 29, 2009

(65) Prior Publication Data
US 2010/0197726 A1 Aug. 5, 2010

(30) Foreign Application Priority Data

Jul. 20, 2007 (JP) ................................ 2007-189858

(51) Int. Cl.
*A01N 43/42* (2006.01)
*A61K 31/47* (2006.01)
*C07D 215/04* (2006.01)
*C07D 215/12* (2006.01)
*C09B 25/00* (2006.01)
*C07F 15/00* (2006.01)

(52) U.S. Cl. ............................ 514/311; 546/173; 546/10
(58) Field of Classification Search .................. 514/311; 546/173, 10
See application file for complete search history.

(56) References Cited

U.S. PATENT DOCUMENTS

2004/0013643 A1  1/2004  Mach
2005/0159615 A1  7/2005  Lifshitz-Liron

FOREIGN PATENT DOCUMENTS

JP   2006 325582   12/2006
WO   2005 063728    7/2005

OTHER PUBLICATIONS

Extended European Search Report issued Nov. 30, 2010, in Application No. / Patent No. 08790226.8-2123 / 2168950 PCT/JP2008001924.
Victor S. Gurevich, et al., "Statins and autoimmune diseases" Autoimmunity Reviews, vol. 4, No. 3, Elsevier, XP-002607497, Mar. 2005, pp. 123-129.
Anonymous: "Marshall Protocol Knowledge Base", Autoimmunity Research Foundation, XP-002607498, Oct. 28, 2010, (Retrieved from the Internet : URL:http://mpkb.org/home/pathogenesis/thIspectrum[hashkey]fn_123>), 5 pages.
Nagayama, Narumi et al., "Induction of a Th2 bias by an anti-cholesterol drug—Is it possible to apply the drug to treatment of multiple sclerosis (MS) ?", Clinical Immunology, vol. 40, No. 2, pp. 205 to 208, (2003), (with partial English translation).
Youssef, Sawsan. et al., "The HMG-CoA reductase inhibitor, atorvastatin, promotes a Th2 bias and reverses paralysis in central nervous system autoimmune disease", Nature, vol. 420, pp. 78-84, Nov. 7, 2002.
Noseworthy, John et al., "Multiple Sclerosis", The New England Journal of Medicine, vol. 343, No. 13, pp. 938-952, Sep. 28, 2000.
Joseph, J. et al., "Down-regulation of interferon-γ-induced class II expression on human glioma cells by recombinant interferon-β:effects of dosage treatment schedule", Journal of Neuroimmunology, vol. 20, No. 1, pp. 39-44, (1988).
The IFNB Multiple Sclerosis Study Group "Interferon beta-1b is effective in relapsing-remitting multiple sclerosis." I. Clinical results of a multicenter, randomized, double-blind, placebo-controlled trial, Neurology, vol. 43, pp. 655-661, (Apr. 1993).
Vollmer, Timothy, et al., "Oral simvastatin treatment in relapsing-remitting multiple sclerosis", The Lancet, vol. 363, pp. 1607-1608, May 15, 2004.

*Primary Examiner* — Samira Jean-Louis
(74) *Attorney, Agent, or Firm* — Oblon, Spivak, McClelland, Maier & Neustadt, L.L.P.

(57) ABSTRACT

The present invention is to provide an inhibitor that inhibits differentiation of T cells into Th1 cells.
The inhibitor that inhibits differentiation of T cells into Th1 cells contains, as an active ingredient, pitavastatin or a salt thereof.

7 Claims, 2 Drawing Sheets

INHIBITOR OF THE DIFFERENTIATION OF T CELLS INTO TH1 CELLS

CROSS-REFERENCE TO RELATED APPLICATIONS

This application is a National Stage of PCT/JP08/001,924 filed Jul. 18, 2008 and claims the benefit of JP 2007-189858 filed Jul. 20, 2007.

TECHNICAL FIELD

The present invention relates to a drug for inhibiting differentiation of T cells into Th1 cells, which plays a central role in the onset and development of, for example, multiple sclerosis, type I diabetes, or rheumatoid arthritis.

BACKGROUND ART

Lymphocytes include T cells, and B cells, which produce antibodies (immunoglobulins). T cells include helper T cells (CD4 antigen positive), which regulate immune response to antigens presented by monocytes or macrophages, and killer T cells (CD8 antigen positive), which destroy, for example, virus-infected cells. Helper T cells include Th1 cells (T helper 1 cells) and Th2 cells (T helper 2 cells). Whether Th1 cells (cellular immunity) or Th2 cells (humoral immunity) are dominant is determined by whether IL-12 or IL-4 is produced by antigen-presenting cells.

Thus, Th1 cells and Th2 cells respectively play an immunological role, and are involved in biological defense. However, it has been known to induce differentiation of T cells into Th1 cells and then excessive activation of Th1 cells may cause various diseases. Diseases known to be caused by excessive induction of Th1 cells include multiple sclerosis, type I diabetes, and rheumatoid arthritis.

Among these diseases, multiple sclerosis is a cryptogenic, intractable disease which is designated as a specified disease by the Japanese Ministry of Health, Labor and Welfare, and this disease involves central dysfunction due to cerebrospinal demyelination and causes sight problems, dyskinesia, etc. In Europe and the United States, the prevalence of multiple sclerosis is higher than that of any other neurological diseases affecting young adults, and is about 50 per 100,000 population. In Japan, the prevalence of multiple sclerosis is estimated to be about 8 or 9 per 100,000 population, and the number of multiple sclerosis patients is estimated to be about 12,000. In many cases, multiple sclerosis involves repeated remissions and relapses (relapsing-remitting multiple sclerosis). Particularly, the onset of multiple sclerosis often occurs around age 30, and relapse of the disease becomes less frequent with increasing age. However, some multiple sclerosis patients exhibit rapid progression of symptoms (chronic progressive multiple sclerosis). It has been shown that T cells or macrophages invade lesion sites of multiple sclerosis patients, and these cells are considered to break myelin protein and myelin sheath in central nerves, thereby causing neurological disorders (Non-Patent Document 1). Demyelinating lesions may be distributed throughout the central nervous system, but are located mainly in, for example, the optic nerves, the brain stem, the spinal cord, and the cerebellum. Multiple sclerosis causes a variety of symptoms (e.g., paralysis of the limbs, shivering, fatigue, optic nerve disorder, dysuria, and dyschezia), and these symptoms vary depending on the site where nerves are damaged.

In current therapy for multiple sclerosis, a steroid is used in the acute phase, whereas an interferon-β (IFN-β) pharmaceutical product or a glatiramer pharmaceutical product is used for prevention of relapse. However, the latter pharmaceutical product is not approved in Japan. An IFN-β pharmaceutical product acts on T cells, to thereby control the amount of interferon-γ produced, and to suppress antigen presentation by antigen-presenting cells (Non-Patent Document 2). Therefore, conceivably, an IFN-β pharmaceutical product suppresses enhancement of immune response, and contributes to delay of progression of multiple sclerosis symptoms or reduction in relapse frequency. However, even when such a pharmaceutical product is administered to multiple sclerosis patients, relapses of multiple sclerosis occur (average relapse frequency: about 0.8 a year), and a method for reliably preventing relapse of multiple sclerosis has not yet been developed (Non-Patent Document 3). In addition, such a pharmaceutical product requires frequent subcutaneous administration, which causes problematic side effects such as fever and subcutaneous ulcer, and imposes a considerable burden on patients in terms of compliance. Therefore, development of a pharmaceutical product which can be orally administered is considered very important for the treatment of multiple sclerosis. Meanwhile, although pulse therapy using cyclophosphamide (i.e., an immunosuppressive agent) has been reported to be effective for patients with severe progressive multiple sclerosis, this agent causes severe side effects (e.g., leukopenia and alopecia), and thus requires careful administration. Under such circumstances, keen demand has arisen for an effective therapeutic method for multiple sclerosis.

Statin compounds (i.e., HMG-Co reductase inhibitors) are known to exhibit various pharmacological effects. It has been known that, for example, atorvastatin and simvastatin are effective for an experimental autoimmune encephalomyelitis (EAE) model; exhibit the effect of inhibiting proliferation of T cells and the effect of inducing differentiation of T cells into Th2 cells; and thus are probably effective for multiple sclerosis (Non-Patent Documents 4 and 5).

Non-Patent Document 1: Noseworthy, et al.; N. Engl. J. Med. Vol. 343, No. 13, pp. 938-52 (2000)
Non-Patent Document 2: Joseph, et al.; J. Neuroimmunol. Vol. 20, No. 1, pp. 39-44 (1988)
Non-Patent Document 3: The IFNB Multiple Sclerosis Study Group; Neurology Vol. 43, No. 4, pp. 655-61 (1993)
Non-Patent Document 4: Nature, 420, 78-84, 2002
Non-Patent Document 5: Lancet, 363, 1607-1608, 2004

DISCLOSURE OF THE INVENTION

Problems to be Solved by the Invention

However, no studies have been conducted on the effects of pitavastatin (i.e., a statin compound) on multiple sclerosis or Th1 cells.

An object of the present invention is to provide a drug which selectively inhibits induction of differentiation of T cells into Th1 cells, and which is useful for the treatment of a disease caused by activation of Th1 cells.

Means for Solving the Problems

In view of the foregoing, the present inventor has conducted extensive studies focusing on pitavastatin (i.e., a statin compound), whose effects on multiple sclerosis or Th1 cells have not yet been elucidated, and as a result has found that pitavastatin or a salt thereof exhibits the effect of inhibiting differentiation of T cells into Th1 cells, which effect is about 10-fold higher than that of atorvastatin, and also exhibits the effect of inhibiting activation of Th1 cells. The present invention has been accomplished on the basis of this finding.

Accordingly, the present invention provides an inhibitor that inhibits differentiation of T cells into Th1 cells, which contains, as an active ingredient, pitavastatin or a salt thereof.

The present invention also provides an inhibitor that inhibits activation of Th1 cells, which contains, as an active ingredient, pitavastatin or a salt thereof.

The present invention also provides a pharmaceutical composition for inhibiting differentiation of T cells into Th1 cells, the composition comprising pitavastatin or a salt thereof, and a pharmaceutically acceptable carrier.

The present invention also provides a pharmaceutical composition for inhibiting activation of Th1 cells, the composition comprising pitavastatin or a salt thereof, and a pharmaceutically acceptable carrier.

The present invention also provides use of pitavastatin or a salt thereof for producing an inhibitor that inhibits differentiation of T cells into Th1 cells.

The present invention also provides use of pitavastatin or a salt thereof for producing an inhibitor that inhibits activation of Th1 cells.

The present invention also provides a method for inhibiting differentiation of T cells into Th1 cells, the method comprising administering pitavastatin or a salt thereof to a subject in need thereof.

The present invention also provides a method for inhibiting activation of Th1 cells, the method comprising administering pitavastatin or a salt thereof to a subject in need thereof.

The present invention also provides pitavastatin or a salt thereof for inhibiting differentiation of T cells into Th1 cells.

The present invention also provides pitavastatin or a salt thereof for inhibiting activation of Th1 cells.

Effects of the Invention

Pitavastatin or a salt thereof exhibits an extremely-marked effect of inhibiting differentiation of T cells into Th1 cells and an extremely-marked effect of inhibiting activation of Th1 cells. Therefore, pitavastatin or a salt thereof is useful as a therapeutic drug for a disease caused by excessive induction of differentiation of T cells into Th1 cells.

BEST MODE FOR CARRYING OUT THE INVENTION

Figure 1:
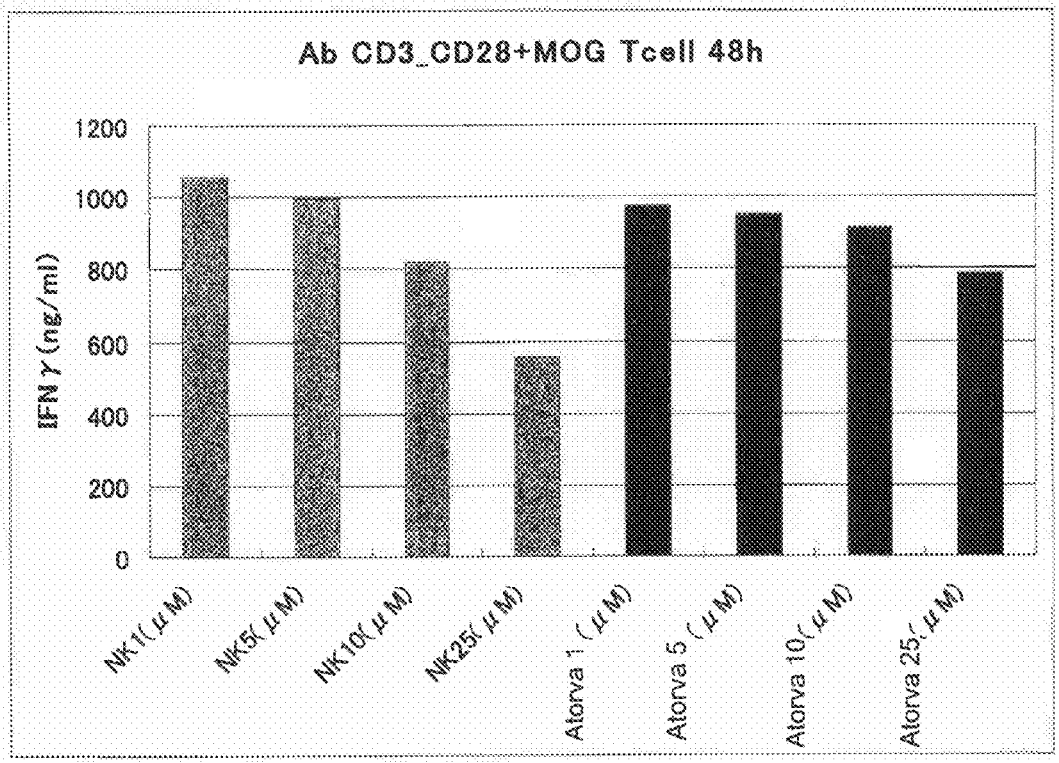
FIG. 1 shows the effect of pitavastatin or atorvastatin on inhibiting activation of Th1 cells (NK: pitavastatin, Atorva: atorvastatin).

The present invention employs pitavastatin (((3R,5S,6E)-7-[2-cyclopropyl-4-(4-fluorophenyl)-3-quinolyl]-3,5-dihydroxy-6-heptenoic acid): U.S. Pat. No. 5,856,336 and JP-A-1989-279866) or a salt thereof. As used herein, "pitavastatin or a salt thereof" also encompasses a hydrate of pitavastatin or a salt thereof, and a solvate of pitavastatin or a salt thereof with a pharmaceutically acceptable solvent. Examples of the salt include alkali metal salts such as a sodium salt and a potassium salt; alkaline earth metal salts such as a calcium salt and a magnesium salt; organic amine salts such as a phenethylamine salt; and ammonium salts. Of these, a salt of pitavastatin is preferred, and a calcium salt is particularly preferred.

Pitavastatin or a salt thereof may be produced through the method described in U.S. Pat. No. 5,856,336 or JP-A-1989-279866.

As described in the Examples hereinbelow, pitavastatin or a salt thereof exhibits the effect of considerably inhibiting induction of differentiation of human T cells into Th1 cells. That is, pitavastatin or a salt thereof inhibits differentiation of T cells into Th1 cells, and markedly improves Th1/Th2 balance. Also, pitavastatin or a salt thereof strongly inhibits activation of Th1 cells. Such effects of pitavastatin are 10-fold higher than those of atorvastatin, which, among statin compounds, has hitherto been suggested to be probably effective for multiple sclerosis. Thus, the effects of pitavastatin are so potent that they cannot be predicted from those of atorvastatin. Therefore, pitavastatin or a salt thereof is useful as a therapeutic drug for a disease caused by differentiation of T cells into Th1 cells or activation of Th1 cells, such as multiple sclerosis, type I diabetes, or rheumatoid arthritis.

No particular limitation is imposed on the dosage form of the drug of the present invention, and the dosage form may be appropriately determined in consideration of the purpose of treatment. For example, the drug may be orally administered in the form of, for example, tablet, capsule, granule, film coating agent, powder, or syrup, or may be parenterally administered in the form of, for example, injection, suppository, inhalant, percutaneous absorption agent, eye drop, or nasal drop. The drug is preferably provided in the form of a peroral product.

A pharmaceutical product suitable for such a dosage form may contain a pharmaceutically acceptable carrier. Examples of the carrier include excipients and extenders such as starches, lactose, sucrose, mannitol, and silicic acid; disintegrating agents such as agar, calcium carbonate, potato or tapioca starch, alginic acid, and composite silicic acid salts; binders such as hydroxypropylmethylcellulose, methylcellulose, sodium carboxymethylcellulose, alginic acid salts, gelatin, polyvinyl pyrrolidone, sucrose, and gum arabic; lubricants such as talc, calcium stearate, magnesium stearate, solid polyethylene glycols, sodium laurylsulfate, and mixtures thereof; diluents such as lactose and cornstarch; buffers such as organic acids (e.g., citric acid, phosphoric acid, tartaric acid, and lactic acid), inorganic acids (e.g., hydrochloric acid), alkali hydroxides (e.g., sodium hydroxide and potassium hydroxide), and organic amines (e.g., triethanolamine, diethanolamine, and diisopropanolamine); antiseptics such as p-hydroxybenzoic acid esters and benzalkonium chloride; emulsifiers such as anionic surfactants (e.g., calcium stearate, magnesium stearate, and sodium laurylsulfate), cationic surfactants (e.g., benzalkonium chloride, benzethonium chloride, and cetylpyridinium chloride), and nonionic surfactants (e.g., glyceryl monostearate, sucrose fatty acid esters, polyoxyethylene hydrogenated castor oil, polyoxyethylene sorbitan fatty acid esters, polyoxyethylene fatty acid esters, and polyoxyethylene alkyl ethers); and stabilizers such as sodium sulfite, sodium hydrogensulfite, dibutylhydroxytoluene, butylhydroxyanisole, and edetic acid. Optionally, the pharmaceutical product may appropriately contain an additional additive (e.g., a flavoring agent, a dispersant, a preservative, or a perfume) in combination with any of the aforementioned carriers.

In the present invention, the dose of pitavastatin or a salt thereof may be appropriately determined in consideration of the body weight, age, sex, symptom, etc. of a patient in need thereof. Generally, the daily dose of pitavastatin or a salt thereof for an adult is 0.01 to 50 mg, preferably 0.1 to 20 mg, more preferably 1 to 10 mg. The daily dose is administered once a day, or in a divided manner (several times a day).

EXAMPLES

The present invention will next be described in more detail by way of examples. However, the technical scope of the present invention is not limited to these examples.

Example 1

(Method)

Five C57BL/6 mice were immunized with myelin oligodendrocyte glycoprotein (MOG), and mice with experimental autoimmune encephalomyelitis (EAE) (i.e., a model of multiple sclerosis) were prepared in a conventional manner. On day 14 after immunization, spleen cells were collected from each mouse and cultured in a 24-well culture plate coated with CD3 and CD28 antibodies, and then stimulated with MOG in the presence of pitavastatin or atorvastatin, to thereby activate Th1 cells. The Th1 cytokine (IFN-γ) concentration of the supernatant of the resultant cell culture was determined through ELISA.

(Results)

As shown in FIG. 1, a concentration of 10 μM or more of pitavastatin ("NK" in FIG. 1) significantly reduced the amount of IFN-γ produced by Th1 cells derived from spleen cells of MOG-immunized mice; i.e., inhibited activation of Th1 cells. As also shown in FIG. 1, 25 μM of atorvastatin ("Atorva" in FIG. 1) significantly inhibited production of IFN-γ by Th1 cells.

Example 2

(Method)

Peripheral blood (10 mL) was collected from six healthy adults in heparin, and monocytes were isolated through the Ficol-Hypaque method (i.e., a customary method). The thus-isolated cells were diluted to $1 \times 10^6$/mL and then inoculated into a 24-well culture plate coated with CD3 and CD28 antibodies (Falcon), followed by culturing for four days in the presence of IL-12 (100 ng/mL), to thereby induce differentiation of T cells into Th1 cells. Atorvastatin or pitavastatin (0.01 to 10 μM) was added at the time of initiation of culturing, and the effect of each drug on differentiation of T cells into Th1 cells was examined. After completion of culturing, cells were washed thrice with PBS, and cytokines (IFN-γ and IL-4) in the cells and CD4 on the surfaces of the cells were stained in a conventional manner. The ratio of Th1 (CD4-positive, IFN-γ-positive cells) or Th2 (CD4-positive, IL-4-positive cells) to all the CD4-positive T cells was determined through flow cytometry.

Specifically, lymphocytes were stimulated with anti-CD3 antibody and anti-CD28 antibody, and the amounts of IFN-γ (Th1 cytokine) and IL-4 (Th2 cytokine) in the cells were determined through flow cytometry, to thereby compare pitavastatin with atorvastatin in terms of the effect of inhibiting differentiation of peripheral blood T cells into Th1 cells, and the effect of promoting differentiation of peripheral blood T cells into Th2 cells.

(Results)

Figure 2:
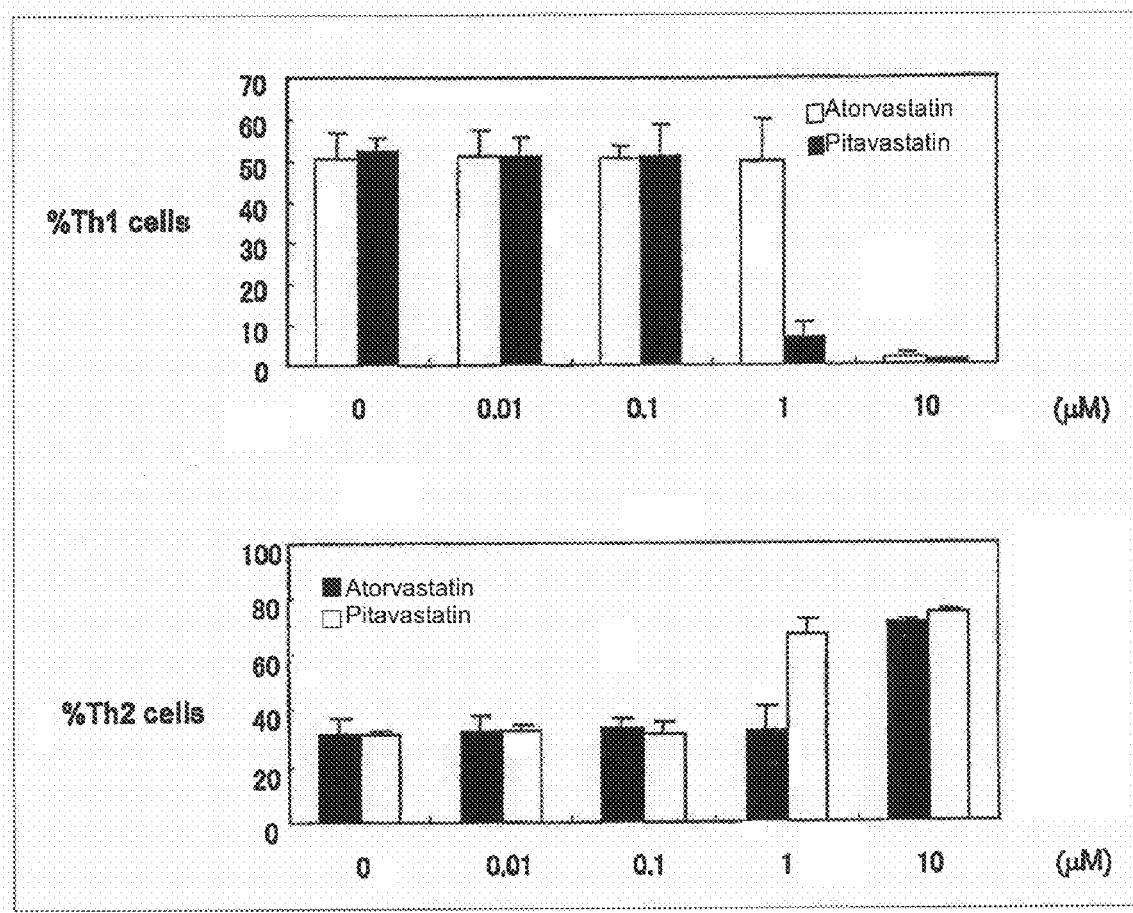
FIG. 2 shows comparison between pitavastatin and atorvastatin in terms of the effect of inhibiting differentiation of T cells into Th1 cells and the effect of promoting differentiation of T cells into Th2 cells.

As shown in FIG. 2, in the case of atorvastatin, at least 10 μM was required to exhibit the effect of inhibiting differentiation of T cells into Th1 cells or the effect of promoting differentiation of T cells into Th2 cells. In contrast, 1 μM of pitavastatin significantly exhibited the effect of inhibiting differentiation of T cells into Th1 cells or the effect of promoting differentiation of T cells into Th2 cells. These data indicated that the effects of pitavastatin in inhibiting differentiation of T cells into Th1 cells and in promoting differentiation of T cells into Th2 cells are 10-fold higher than those of atorvastatin.

The aforementioned data (the above-determined amount of IFN-γ produced) indicated that the effect of pitavastatin on activation of Th1 cells is 2.5-fold higher than that of atorvastatin on inhibiting activation of Th1 cells (FIG. 1).

Comparison between pitavastatin and atorvastatin in terms of the effect of inhibiting differentiation of human T cells into Th1 cells and the effect of promoting differentiation of human T cells into Th2 cells showed that pitavastatin inhibits differentiation of T cells into Th1 cells or promotes differentiation of T cells into Th2 cells 10-fold more strongly than does atorvastatin; i.e., the Th1/Th2 ratio improving effect of pitavastatin is 10-fold higher than that of atorvastatin (FIG. 2).

The invention claimed is:

1. A method for inhibiting differentiation of T cells into Th1 cells, the method comprising administering pitavastatin or a salt thereof to a subject in need thereof.

2. The method of claim 1, wherein a pitavastatin salt is administered.

3. The method of claim 2, wherein the pitavastatin salt is pitavastatin calcium salt.

4. The method of claim 1, wherein the pitavastatin or a salt thereof is administered in a daily dose of 0.01 to 50 mg.

5. The method of claim 1, wherein the pitavastatin or a salt thereof is administered in a daily dose of 0.1 to 20 mg.

6. The method of claim 1, wherein the pitavastatin or a salt thereof is administered in a daily dose of 1 to 10 mg.

7. The method of claim 1, wherein the pitavastatin or a salt thereof is administered in a composition that comprises one or more pharmaceutically acceptable carriers.

\* \* \* \* \*